United States Patent
Krebs et al.

(10) Patent No.: US 8,343,956 B2
(45) Date of Patent: Jan. 1, 2013

(54) PROCESS FOR MAKING A CRYSTALLINE ZILPATEROL SALT

(75) Inventors: Oliver Krebs, Visp (CH); Philipp Kuenti, Visp (CH); Christoph Michlig, Visp (CH); Karl Reuter, Freiburg (DE)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 13/039,455

(22) Filed: Mar. 3, 2011

(65) Prior Publication Data
US 2012/0058189 A1 Mar. 8, 2012

Related U.S. Application Data

(63) Continuation of application No. 12/841,700, filed on Jul. 22, 2010, now abandoned, which is a continuation of application No. 12/639,082, filed on Dec. 16, 2009, now abandoned.

(60) Provisional application No. 61/138,310, filed on Dec. 17, 2008.

(30) Foreign Application Priority Data

Dec. 17, 2008 (EP) .................................... 08171966

(51) Int. Cl.
*A61K 31/55* (2006.01)
*C07D 487/06* (2006.01)

(52) U.S. Cl. .................................. 514/214.02; 540/579

(58) Field of Classification Search ............. 514/214.02; 540/579
See application file for complete search history.

(56) References Cited

U.S. PATENT DOCUMENTS

| | | | |
|---|---|---|---|
| 4,585,770 A | 4/1986 | Frechet et al. | |
| 4,900,735 A | 2/1990 | Grandadam | |
| 5,731,028 A | 3/1998 | Chevremont et al. | |
| 5,847,124 A * | 12/1998 | Chevremont et al. | ......... 540/579 |
| 7,207,289 B2 | 4/2007 | Montgomery | |
| 7,921,060 B2 | 4/2011 | Alsup et al. | |
| 2005/0284380 A1 | 12/2005 | Montgomery | |
| 2008/0267942 A1 | 10/2008 | Boyle et al. | |
| 2009/0181906 A1 | 7/2009 | Wray et al. | |
| 2010/0022490 A1 | 1/2010 | Miculka et al. | |
| 2010/0121050 A1 | 5/2010 | Dubuis | |
| 2010/0173892 A1 | 7/2010 | Almena-Perea et al. | |
| 2011/0184859 A1 | 7/2011 | Alsup et al. | |

FOREIGN PATENT DOCUMENTS

| | | |
|---|---|---|
| EP | 0 107 569 A1 | 5/1984 |
| EP | 0 753 518 A1 | 1/1997 |
| WO | 2008/119754 A1 | 10/2008 |

OTHER PUBLICATIONS

Kumar et al., "Role of Additives like Polymers and Surfactants in the Crystallization of Mebendazole", Yakugaku Zasshi, The Pharmaceutical Society of Japan, 2008, pp. 281-289, vol. 128, No. 2.

Mullin, J. W., "Crystallization", 2001, pp. 400-401, Elsevier Butterworth-Heinemann, XP002547716.

von Bonsdorff-Nikander at al., "Optimizing the Crystal Size and Habit of β-Sitosterol in Suspension", AAPS PharmSciTech, 2003, pp. 1-8, vol. 4, No. 3.

International Search Report for corresponding PCT application PCT/EP2009/067316, mailed on Mar. 11, 2010.

* cited by examiner

*Primary Examiner* — Brenda Coleman
(74) *Attorney, Agent, or Firm* — David J. Kerwick

(57) ABSTRACT

This invention generally relates to processes for making a crystalline zilpaterol salt, particularly zilpaterol hydrochloride. This invention also relates to methods of treatment using a crystalline zilpaterol salt prepared in accordance with this invention to increase the rate of weight gain, improve feed efficiency, and/or increase carcass leanness in livestock, poultry, and fish.

23 Claims, No Drawings

PROCESS FOR MAKING A CRYSTALLINE ZILPATEROL SALT

This application is a continuation of U.S. patent application Ser. No. 12/841,700 filed Jul. 22, 2010, now abandoned which is a continuation of U.S. patent application Ser. No. 12/639,082, filed Dec. 16, 2009, now abandoned which claims the benefit of U.S. Provisional Patent Application Ser. No. 61/138,310 filed Dec. 17, 2008.

FIELD OF THE INVENTION

This invention generally relates to processes for making a crystalline zilpaterol salt, particularly zilpaterol hydrochloride. This invention also relates to methods of treatment using a crystalline zilpaterol salt prepared in accordance with this invention to increase the rate of weight gain, improve feed efficiency, and/or increase carcass leanness in livestock, poultry, and fish.

BACKGROUND OF THE INVENTION

Zilpaterol is a known racemic adrenergic β-2 agonist having the following structure:

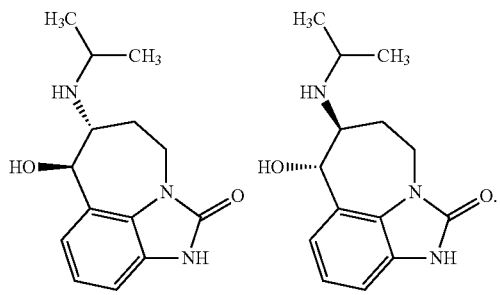

The CAS name is trans-(±)-4,5,6,7-tetrahydro-7-hydroxy-6-[(1-methylethyl)amino]-imidazo[4,5,1-jk][1]benzazepin-2(1H)-one.

It is well known that zilpaterol, various zilpaterol derivatives, and various pharmaceutically acceptable salts of zilpaterol and its derivatives may, for example, be used to increase the rate of weight gain, improve feed efficiency (i.e., decrease the amount of feed per amount of weight gain), and/or increase carcass leanness (i.e., increase protein content in carcass soft tissue) in livestock, poultry, and/or fish.

In U.S. Pat. No. 4,900,735, for example, Grandadam describes zootechnical compositions of racemic trans zilpaterol and salts thereof that may be used to increase the weight and meat quality of warm-blooded animals, including cattle, pigs, and poultry. And U.S. Patent Appl. Publ. US2005/0284380 describes use of an ionophore/macrolide/zilpaterol dosing regimen to increase beef production, reduce feed intake while maintaining beef production, and reduce incidences of liver abscess in cattle.

Methods for making zilpaterol and salts thereof are known in the art. For example, in U.S. Pat. No. 4,585,770, Frechet et al. describe compounds (and salts thereof) encompassed by a genus characterized as 6-amino-7-hydroxy-4,5,6,7-tetrahydro-imidazo[4,5,1-jk][1]-benzazepin-2[H]-one derivatives and pharmaceutically acceptable acid addition salts thereof. The derivatives correspond in structure to the following formula:

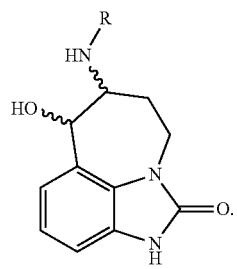

Here, R can be various substituents, and the wavy lines indicate that the bonds to the 6-amino and 7-OH groups have the trans configuration. This genus encompasses racemic trans zilpaterol when R is isopropyl.

Int'l Patent Appl. Publ. WO 2008/119754 discusses making an acid addition salt of zilpaterol free base by mixing the free base with an inorganic or organic acid using various methods known in the art, and specifically mentions HCl.

U.S. Pat. No. 4,585,770 and Int'l Patent Appl. Publ. WO 2008/119754 also discuss the preparation of zilpaterol hydrochloride by dissolving zilpaterol free base in ethanol, adding ethyl acetate saturated with HCl, vacuum-filtering the product to obtain crude zilpaterol hydrochloride, dissolving the crude zilpaterol hydrochloride in hot methanol, adding ethyl acetate, and then filtering to obtain a final zilpaterol hydrochloride product.

Int'l Patent Appl. Publ. WO 2008/119754 also describes processes for making zilpaterol and salts thereof. In some such processes, for example, zilpaterol is prepared from 4-(2-oxo-2,3-dihydrobenzimidazol-1-yl)butyric acid using the following generic scheme:

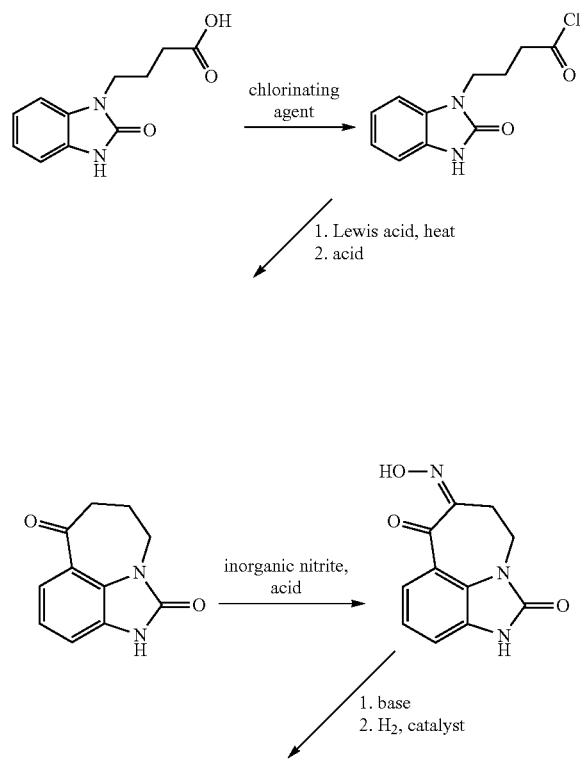

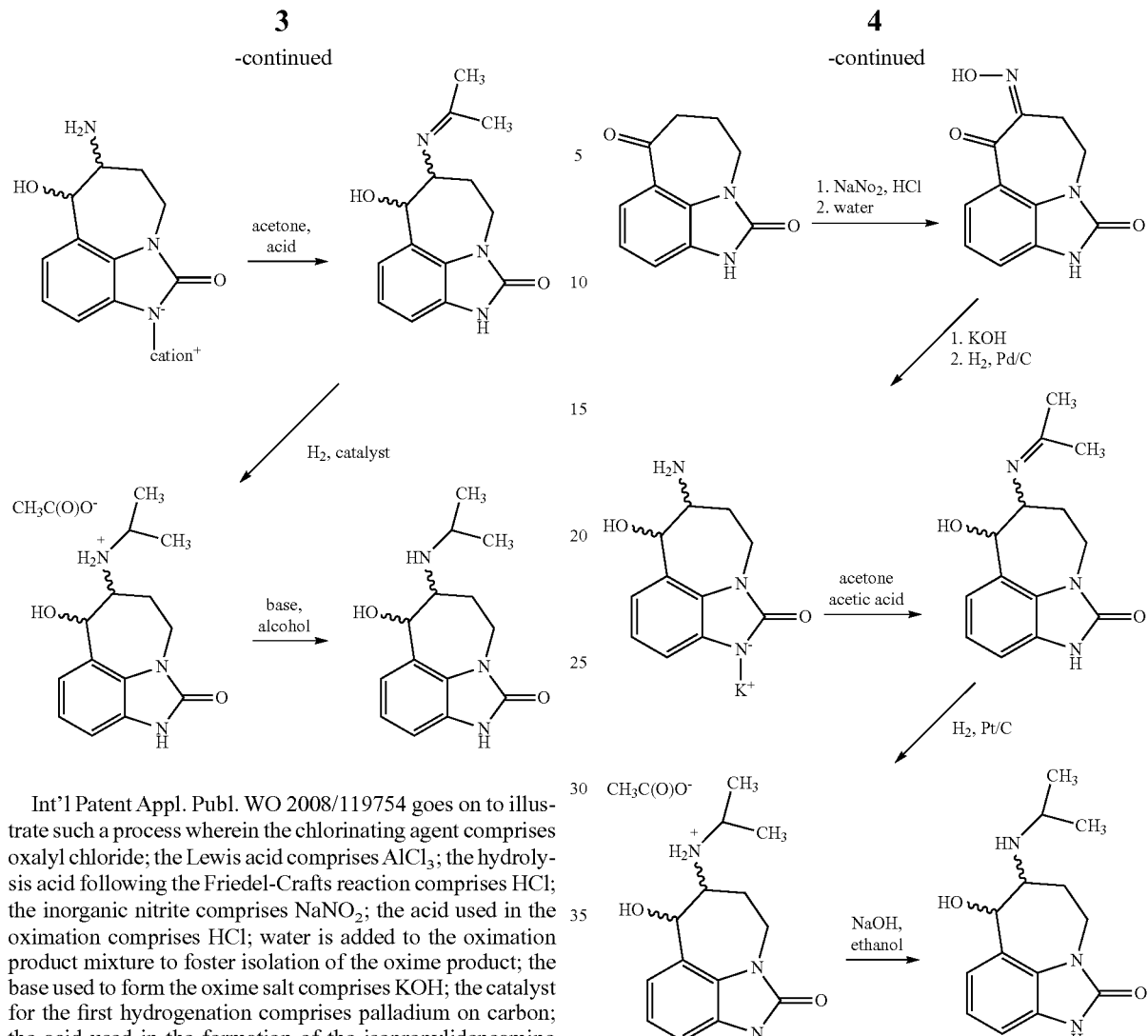

Int'l Patent Appl. Publ. WO 2008/119754 goes on to illustrate such a process wherein the chlorinating agent comprises oxalyl chloride; the Lewis acid comprises $AlCl_3$; the hydrolysis acid following the Friedel-Crafts reaction comprises HCl; the inorganic nitrite comprises $NaNO_2$; the acid used in the oximation comprises HCl; water is added to the oximation product mixture to foster isolation of the oxime product; the base used to form the oxime salt comprises KOH; the catalyst for the first hydrogenation comprises palladium on carbon; the acid used in the formation of the isopropylideneamino compound comprises acetic acid; the catalyst for the second hydrogenation comprises platinum on carbon; and the base and alcohol used to form the zilpaterol free base comprise NaOH and ethanol, respectively:

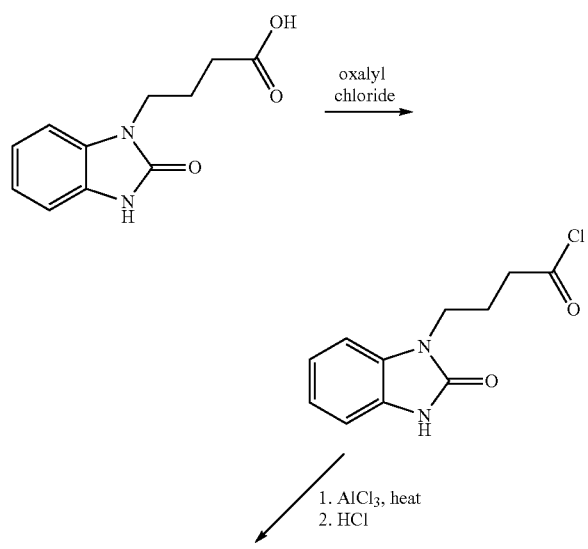

For some applications, it is desirable for zilpaterol or a salt thereof to be in the form of crystals having one or more characteristics, such as a specific size distribution. For example, U.S. Pat. No. 5,731,028 discusses the desirability of a particular crystal size distribution when crystalline zilpaterol hydrochloride is used with 300-800 μm corn cob supports. In that context, U.S. Pat. No. 5,731,028 discusses the desirability of zilpaterol hydrochloride crystals that are less than 300 μm in size, with the majority being from 50 to 200 μm. U.S. Pat. No. 5,731,028 also discusses a desirability to avoid particle sizes so small that that the particles appear in the form of dust, particularly where there is a possibility that such dust could endanger the environment or irritate or poison a user by penetrating the user's pulmonary alveoli. U.S. Pat. No. 5,731,028 specifically discloses crystalline anhydrous zilpaterol hydrochloride having a crystal size distribution wherein less than 5% of the crystals are less than 15 μm, and at least 95% of the crystals are less than 250 μm.

U.S. Pat. No. 5,731,028 discusses various crystallization processes to obtain a desired zilpaterol hydrochloride crystal size distribution that may, for example, be useful with 300-800 μm corn cob supports. These processes include the following various alternatives:

a) Form a supersaturated solution of zilpaterol hydrochloride in water or aqueous ethanol at a temperature greater than 50° C., cool the supersaturated solution to effect crystallization to zilpaterol hydrochloride monohydrate, further cool the solution to a temperature of less than 20° C. to effect crystallization of zilpaterol hydrochloride trihydrate, and dry the hydrated crystals to form the desired crystalline zilpaterol hydrochloride.

b) Dissolve zilpaterol hydrochloride in a minimum of water at 60-100° C., pour the resulting solution into a saturated solution of zilpaterol hydrochloride in aqueous ethanol, seed the mixture with zilpaterol hydrochloride trihydrate crystals while stirring at a temperature of less than 20° C., and dry the resulting zilpaterol hydrochloride trihydrate crystals to form the desired crystalline zilpaterol hydrochloride.

c) Form a saturated aqueous zilpaterol hydrochloride solution by dissolving anhydrous zilpaterol hydrochloride in water at a temperature of less than 30° C. to spontaneously form zilpaterol hydrochloride crystals, and dry the resulting zilpaterol hydrochloride trihydrate crystals to form the desired crystalline zilpaterol hydrochloride.

In view of the importance of zilpaterol salts in animal production, there continues to be a need for more cost-effective, greater yielding, and/or more selective processes for making crystalline zilpaterol salts, particularly crystalline zilpaterol hydrochloride. The following disclosure addresses this need.

SUMMARY OF THE INVENTION

This invention relates to processes for making crystalline zilpaterol salts, particularly crystalline zilpaterol hydrochloride.

Benefits of this crystallization process are a favorably low number of process steps and therefore an increase of yield, desirable purity levels, and, especially, a desirable selectivity with respect to the crystal size of the resulting zilpaterol salt (particle size distribution).

This selectivity in particle size distribution results in a product that is technologically very desirable because it avoids on one hand fine particles that create dust during handling of the product that contains active ingredient. This would be beneficial because it improves the handler safety. On the other hand the avoidance of too big particles allows the homogeneous adhesion of the zilpaterol salt crystals to a support (e.g. corn cob) to ease the formulation of the final product. By this a more homogeneous finished product can be achieved.

Briefly, this invention is directed, in part, to a process for making a crystalline zilpaterol salt. The process comprises forming a mixture by combining a surfactant with water and a zilpaterol salt. The water and zilpaterol salt may be partially (or, more typically, entirely) in the form of an aqueous zilpaterol salt solution.

This invention also is directed, in part, to a process for making a pharmaceutical composition. The process comprises preparing a crystalline zilpaterol salt by a process recited above, and attaching the crystalline zilpaterol salt to a support.

This invention also is directed, in part, to a method of feeding an animal. This method comprises feeding to an animal (e.g., a bovine animal, a swine animal, or a bird) a crystalline zilpaterol salt made by a process described above. Such feeding methods may be used, for example, to increase the animal's rate of weight gain, improve the animal's feed efficiency, and/or increase the animal's carcass leanness.

This invention also is directed, in part, to a use of a crystalline zilpaterol salt, made by a process described above, to make a medicament. Uses for such a medicament include increasing an animal's rate of weight gain, improving an animal's feed efficiency, and/or increasing an animal's carcass leanness.

Specifically the current invention is directed to a process for making a crystalline zilpaterol salt, wherein the process comprises forming a mixture by combining a surfactant with water and a zilpaterol salt wherein the process further comprises seeding the mixture with crystalline zilpaterol hydrochloride trihydrate after decreasing the temperature.

Such process, wherein:
a) a zilpaterol salt solution is formed by a process comprising forming a suspension by a process comprising mixing zilpaterol with water, optionally in the presence of an acid solution, and heating the suspension;
b) the zilpaterol salt solution is mixed with a surfactant;
c) the mixture is seeded with crystalline zilpaterol hydrochloride trihydrate.

Such process, wherein the surfactant is a non-ionic surfactant. Such process, wherein the acid comprises aqueous hydrochlorid acid.

Such process, wherein the crystalline zilpaterol salt comprises crystalline zilpaterol hydrochloride anhydrate.

Such process, wherein the mixture has a temperature of from about −5 to about 5° C. for at least a portion of the process in which zilpaterol hydrochloride trihydrate crystals are present.

Such process, wherein the process further comprises drying a cake comprising zilpaterol hydrochloride trihydrate crystals at a temperature of from about 50 to about 75° C.

Such process, wherein the mixture is first seeded with zilpaterol hydrochloride monohydrate and then with crystalline zilpaterol hydrochloride trihydrate Such process wherein the mixture has a temperature of from about 14 to about 25° C. for at least a portion of the process in which zilpaterol hydrochloride monohydrate crystals are present.

Such process, wherein the zilpaterol hydrochloride crystals have a size distribution in which at least about 95% of the crystal particles have particle sizes that are greater than about 15 μm.

Such process, wherein the zilpaterol hydrochloride crystals have a size distribution in which at least about 90% of the crystal particles have particle sizes that are less than about 200 μm.

Such process, wherein the zilpaterol hydrochloride crystals have a size distribution in which at least about 95% of the crystal particles have particle sizes that are less than about 250 μm.

Such process, wherein the zilpaterol hydrochloride crystals have a size distribution in which at least about 99.5% of the crystal particles have particle sizes that are less than about 300 μm.

Such process, wherein the process further comprises reacting a salt of trans-7-amino-6-hydroxy-6,7,8,9-tetrahydro-2H-2,9a-diazabenzo[cd]azulen-1-one with acetone in the presence of acetic acid.

Such process, wherein the trans-7-amino-6-hydroxy-6,7,8,9-tetrahydro-2H-2,9a-diazabenzo[cd]azulen-1-one salt comprises a potassium salt.

A process for making a pharmaceutical composition, wherein the process comprises:
preparing a crystalline zilpaterol salt by a process as described above; and attaching the crystalline zilpaterol salt to a support.

Such process, wherein the support comprises a corn cob support.

Such process, wherein the support comprises discrete particles having sizes of from about 300 to about 800 μm.

Such process, wherein the crystalline zilpaterol salt comprises crystalline zilpaterol hydrochloride.

A method for increasing an animal's rate of weight gain, improving an animal's feed efficiency, and/or increasing an animal's carcass leanness, wherein the method comprises: preparing a crystalline zilpaterol salt by a process as described above; and administering an effective amount of the crystalline zilpaterol salt to the animal.

Such method, wherein the animal comprises a swine animal.

Such method, wherein the animal comprises a bovine animal.

Such method, wherein at least a portion of the crystalline zilpaterol salt is attached to a support.

Such method, wherein the crystalline zilpaterol salt comprises crystalline zilpaterol hydrochloride. Use of an effective amount of a crystalline zilpaterol salt to manufacture a medicament for increasing an animal's rate of weight gain, improving an animal's feed efficiency, and/or increasing an animal's carcass leanness, wherein the crystalline zilpaterol salt is prepared by a process as described above.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

A. Formation of Crystalline Zilpaterol Salt

In general, this invention is directed to making a crystalline zilpaterol salt (particularly zilpaterol hydrochloride) from an aqueous solution of the salt using a process comprising a surfactant assisted crystallization. To illustrate this invention, the following discussion describes the use of the invention to make crystalline zilpaterol hydrochloride. The principles in this discussion, however, are generally adaptable for preparing other zilpaterol salts.

In some embodiments, the aqueous zilpaterol hydrochloride solution is prepared by first forming a water suspension of zilpaterol hydrochloride. Such a suspension may be prepared by, for example, combining zilpaterol free base with aqueous HCl. In some embodiments, the aqueous HCl comprises from about 12 to about 17% HCl, such as from about 12 to about 15% HCl by weight or from about 13 to about 14% HCl by weight (e.g., about 13.5% by weight). The zilpaterol free base may, for example, be combined directly with an aqueous HCl solution having the desired HCl concentration, or by combining a more-concentrated aqueous HCl solution (e.g., a solution comprising about 33% HCl by weight) with zilpaterol free base in water. In some embodiments, the zilpaterol free base is combined with aqueous HCl at a temperature of no greater than about 30° C., such as from about zero to about 25° C. or from about 5 to about 25° C. (e.g., about 10° C. or 15° C.). The resulting suspension, in turn, may be converted into a solution by heating the suspension to a temperature of at least about 30° C., such as from about 45 to about 100° C., from about 45 to about 85° C., from about 50 to about 70° C., or from about 60 to about 70° C. (e.g., about 65° C.). The heating continues until a clear solution is achieved.

Regardless of how the aqueous zilpaterol hydrochloride solution is prepared, the pH is generally no greater than about 4, and, in some embodiments, no greater than about 2. If the pH is greater than the desired level, acid may be added to reduce the pH. In some embodiments, the acid comprises HCl.

In some embodiments, the aqueous zilpaterol hydrochloride solution is filtered, particularly where the solution appears cloudy. In general, this filtration is conducted until the product solution is clear. Additional water may be used to rinse the filter. This water, in turn, may be added to the product solution.

The concentration of zilpaterol hydrochloride in the solution (particularly following any pH adjustment and/or filtration) is generally at least about 23% by weight, such as from about 23 to about 27% by weight or from about 25 to about 27% by weight (e.g., about 26% by weight). If necessary, water may be added or removed (e.g., by distillation) to achieve the desired concentration. Applicants have discovered in accordance with this invention that a concentration in these ranges (particularly 26% by weight) tends to be beneficial in minimizing the number of undesirably large particles in the final product.

In general, after the zilpaterol hydrochloride solution has been prepared, a surfactant is added. The surfactant may be a non-ionic surfactant or mixtures of non-ionic surfactants. A non-ionic surfactant is a surfactant without a charged moiety. Such non-ionic surfactant can be based on polyethyleneglycol e.g. such as Tween-type surfactants (Polysorbates, Sorbitan esters, poly(oxy-1,2ethanediyl) derives, Tweens). Tween-type surfactants are water soluble nonionic surface active agents comprised of complex esters and ester-ethers derived from hexahydric alcohols, alkylene oxides and fatty acids by adding polyoxyethylene chains to hydroxyl of sorbitol and hexitrol anhydrides (hexitans and hexides) derived from sorbitol and then partially esterifying with the common fatty acids such as lauric, palmitic, stearic and oleic acids.

In one embodiment the Tween-type surfactant is selected from one or more of Tween 20, Tween 40, Tween 60 or Tween 80, also known in the pharmaceutical industry as polysorbate 20, polysorbate 40, polysorbate 60 and polysorbate 80. Polysorbate 20 (Polyoxyethylated Sorbitan Monolaurate,) is a laurate ester, Polysorbate 40 (Polyoxyethylated Sorbitan Monopalmitate), Polysorbate 60 (Polyoxyethylated Sorbitan Monostearate) is a mixture of stearate and palmitate esters; and Polysorbate 80 (Polyoxyethylated Sorbitan Monooleate) is an oleate ester. Such Tween type surfactants are commercially available and/or can be prepared by techniques known in the art.

The surfactant may be, for example, polyethylene glycol sorbitan monostearate. Examples of polyethylene glycol sorbitan monostearate include polysorbate 60 (also known as "Kotilen-1/S" or "Tween® 60").

In some embodiments, the surfactant concentration in the resulting mixture is no greater than about 4% by weight. In some such embodiments, for example, the resulting surfactant concentration in the mixture is from about 0.1 to about 3.9% by weight, such as from about 0.5 to about 3.5% by weight, from about 1.0 to about 3.0% by weight, or from about 1.5 to about 2.5% by weight (e.g., about 2.0% by weight or 0.5% by weight). In some embodiments, the ratio of surfactant to zilpaterol hydrochloride is no greater than about 37 g/mol. In some embodiments, the ratio is from about 3 to about 41 ml/mol, from about 6 to about 23 ml/mol, from about 12 to about 23 ml/mol, from about 14 to about 20 ml/mol (e.g., about 18 ml/mole).

In some embodiments, the temperature of the solution during the surfactant addition is greater than about 45° C., such as from about 60 to about 100° C., from about 50 to about 85° C., from about 50 to about 70° C., or from about 60 to about 70° C., or from 55 to 76° C. (e.g., about 65° C.).

After adding surfactant, seed crystals are typically introduced. In some embodiments, zilpaterol hydrochloride monohydrate seed crystals are used. Zilpaterol hydrochloride monohydrate seed crystals generally tend to be in the form of needles. The amount of zilpaterol hydrochloride monohydrate seed crystals is generally at least about 0.01 g/kg (grams crystals per kg mixture), such as from about 0.01 to about 0.2 g/kg, from about 0.02 to about 0.1, from about 0.02 to about 0.08 g/kg, or from about 0.03 to about 0.05 g/kg (e.g., about 0.04 g/kg). In some embodiments, the ratio of zilpaterol hydrochloride monohydrate seed crystals to zilpaterol hydrochloride is at least about 0.01 g/mol. In some embodiments, the ratio is from about 0.01 to about 0.17 g/mol, from about 0.015 to about 0.12 g/mol, from about 0.025 to about 0.06 mg/mol, or from about 0.038 to about 0.041 mg/mol (e.g., about 0.04 g/mole).

Before, during, and/or after the introduction of zilpaterol hydrochloride monohydrate seed crystals, the temperature of the mixture is typically cooled. In some embodiments, regardless of whether the mixture is cooled before and/or during the zilpaterol hydrochloride monohydrate seeding, the temperature of the mixture during at least a portion (and typically all) of the seeding is at least about 40° C. In some embodiments, the temperature of the mixture during at least a portion (and typically all) of the zilpaterol hydrochloride monohydrate seeding is from about 40 to about 60° C., from about 40 to about 55° C., or from about 40 to about 50° C., or from about 48 to about 55° C. (e.g., about 45° C. or 50° C.). In some embodiments, the seeded mixture is maintained at this temperature following seeding for at least about 5 minutes, such as, for example, for from about 10 to about 30 minutes or from about 10 to about 20 minutes (e.g., 15 or 30 minutes). During at least a portion (and, in some embodiments substantially all or all) this period, the mixture may be stirred. In general, this results in the formation of a white suspension.

After seeding zilpaterol hydrochloride monohydrate crystals, the temperature is generally decreased to a temperature of less than about 40° C. In some embodiments, the temperature is decreased to a temperature of from about 14 to about 35° C., from about 14 to about 25° C., from about 17 to about 23° C., or from about 18 to about 21° C. (e.g., about 21° C. or 18° C.). Applicants have discovered in accordance with this invention that use of a temperature in this range (particularly about 21° C.) tends to be beneficial in minimizing premature trihydrate nuclei formation. In some embodiments, this cooling occurs over an extended time period. In some such embodiments, this period is at least about 5 minutes, such as, for example, from about 5 minutes to about 10 hours, from about 10 minutes to about 5 hours, from about 30 minutes to about 5 hours, or from about 1 to about 2 hours (e.g., about 90 minutes).

Alternatively only zilpaterol hydrochloride trihydrate crystals are seeded without pre-seeding with zilpaterol hydrochloride monohydrate crystals.

After seeding zilpaterol hydrochloride monohydrate crystals, the mixture is typically further seeded with zilpaterol hydrochloride trihydrate crystals. Such trihydrate crystals generally tend to be in the form of prisms. In some embodiments such trihydrate crystals are micronized, i.e. the size of such solid material's particles is reduced to only a few microns in diameter. It can be shown that the seeding of zilpaterol hydrochloride trihydrate crystals mainly causes zilpaterol hydrochloride monohydrate crystals in the mixture to transform into zilpaterol hydrochloride trihydrate crystals. A partial transformation of monohydrate crystals to trihydrate crystals also may occur before the trihydrate seeding. The amount of zilpaterol hydrochloride trihydrate seed crystals introduced into the mixture is generally at least about 0.07 g/kg (grams seed crystals per kg mixture), such as from about 0.07 to about 2 g/kg, from about 0.1 to about 1 g/kg, from about 0.15 to about 0.6 g/kg, or from about 0.2 to about 0.33 g/kg (e.g., about 0.3 g/kg). Applicants have discovered in accordance with this invention that a concentration in these ranges (particularly 0.3 g/kg) tends to be beneficial in minimizing the number of undesirably large particles in the final product. In some embodiments, the ratio of zilpaterol hydrochloride trihydrate seed crystals to zilpaterol hydrochloride is at least about 0.06 mg/mol. In some embodiments, the ratio is from about 0.06 to about 0.6 g/mol, from about 0.16 to about 0.38 g/mol, or from about 0.29 to about 0.36 mg/mol (e.g., about 0.34 g/mole).

In some embodiments, the mixture is aged for a period of time after the seeding of zilpaterol hydrochloride trihydrate seed crystals. In some such embodiments, for example, the aging period is at least about 5 minutes, such as, for example, from about 5 minutes to about 20 hours, from about 30 minutes to about 15 hours, from about 1 to about 15 hours, from about 1 to about 10 hours, or from about 1 to about 4 hours or from about 1.5 to about 3 hours (e.g., about 2 hours). In some such embodiments, the mixture is maintained during at least a portion (and, in some embodiments, substantially all or all) of the aging period at a temperature of less than about 40° C., such as from about 14 to about 35° C., from about 14 to about 25° C., from about 17 to about 23° C., or from about 18 to about 21° C. or from about 17 to about 20° C. (e.g., about 21° C. or 18° C.). In some embodiments, the temperature during at least part (or, in some embodiments, substantially all or all) of the aging period falls within the same temperature range used during the seeding of the zilpaterol hydrochloride trihydrate seed crystals.

In some embodiments, the mixture is cooled after the addition of zilpaterol hydrochloride trihydrate seed crystals (and an aging period, to the extent an aging period is used). In some such embodiments, for example, the mixture is cooled to a temperature of no greater than about 25° C. or no greater than about 15° C., such as from about −5 to about 5° C., from about −2 to about 4° C., or from about zero to about 2° C. (e.g., about 2° C. or 0° C.).

The zilpaterol hydrochloride trihydrate crystals in the product mixture may be recovered by various methods. Such methods include those known in the art, such as, for example, filtration or centrifugation. Typically, the crystals are washed with an acceptable agent, such as, for example, acetone, following the recovery.

The resulting wet zilpaterol hydrochloride trihydrate cake generally may be dried to form crystalline anhydrous zilpaterol hydrochloride. The resulting crystalline anhydrous zilpaterol hydrochloride is generally in the form of prisms.

In some embodiments, the zilpaterol hydrochloride trihydrate cake undergoes an initial drying by being heated under an inert (e.g., a nitrogen or argon) atmosphere to a temperature of greater than 25° C. In general, the temperature of this initial heating is no greater than about 40° C. In some embodiments, for example, the temperature is from about 28 to about 35° C. (e.g., about 30° C.). This initial drying may be conducted over a range of pressures, including atmospheric pressure (absolute), less than atmospheric pressure, and greater than atmospheric pressure. Typically, however, the drying is conducted at a pressure that is no greater than atmospheric pressure, and, in some embodiments, less than atmospheric pressure. It also may occur under a constant flow of the inert gas. In some embodiments, the cake is heated in this manner until the water content in the cake is no greater than about 16%.

After the water content in the cake has been decreased (e.g., to a concentration of no greater than about 16%), the cake is generally dried at a temperature that is greater than about 40° C. to form crystalline anhydrous zilpaterol hydrochloride. In some embodiments, for example, the cake is heated to a temperature of from about 50 to about 75° C. or from about 55 to about 65° C. (e.g., about 60° C.). This further heating typically occurs under an inert atmosphere (e.g., nitrogen or argon), which, in some embodiments, has generally the same atmosphere composition as the initial heating. In general, the heating may be conducted over a range of pressures, including atmospheric, less than atmospheric, and greater than atmospheric pressure. Typically, however, it is conducted at a pressure that is no greater than atmospheric pressure, and, in some embodiments, less than atmospheric pressure. In some embodiments, the heating is continued until the water content in the resulting solids is no greater than about 1%.

The crystallization process of this invention may generally be conducted with various types of reactors. The reactor preferably has a surface that is stable when exposed to the crystallization conditions may be used. Such reactors may include, for example, glass and glass-lined reactors. Other reactors may include, for example, stainless steel or other corrosion-resistant metal alloy reactors.

In some embodiments, the above process makes crystals having a size distribution wherein at least one of the following is satisfied:

a) At least about 95% of the crystal particles have particle sizes that are greater than about 15 μm.

b) At least about 90% of the crystal particles have particle sizes that are less than about 200 μm.

c) At least about 99.5% of the crystal particles have particle sizes that are less than about 300 μm.

In some embodiments, the process makes crystals having a size distribution wherein at least two (or, in some embodiments, all three) of the above criteria are satisfied.

B. Synthesis of Zilpaterol Free Base

The zilpaterol free base used in the above process may be synthesized using various processes. As noted above in the Background of the Invention section, such processes include, for example, the processes discussed in U.S. Pat. No. 4,585,770. Such processes also include, for example, those discussed in Int'l Patent Appl. Publ. WO 2008/119754.

In some embodiments, the process for making zilpaterol free base comprises deprotonating 8,9-dihydro-2H-2,9a-diazabenzo[cd]azulene-1,6,7-trion-7-oxime with a base in water to form a 2H-2,9a-diazabenzo[cd]azulene-1,6,7-trion-7-oxime salt that goes into solution, and then hydrogenating the salt in the presence of a catalyst to form the corresponding racemic trans-7-am no-6-hydroxy-6,7,8,9-tetrahydro-2H-2, 9a-diazabenzo[cd]azulen-1-one salt as follows (the wavy lines represent the trans configuration):

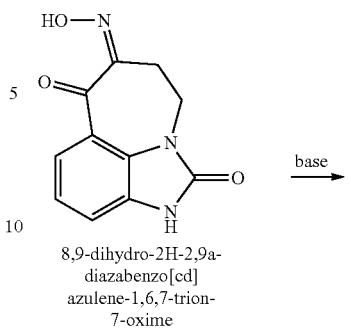

8,9-dihydro-2H-2,9a-diazabenzo[cd]azulene-1,6,7-trion-7-oxime base →

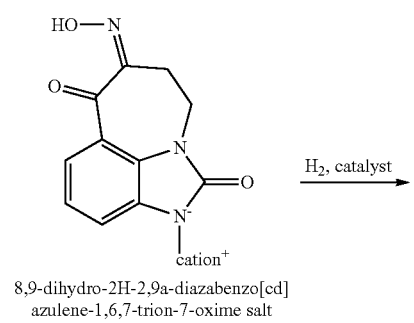

8,9-dihydro-2H-2,9a-diazabenzo[cd]azulene-1,6,7-trion-7-oxime salt

H$_2$, catalyst →

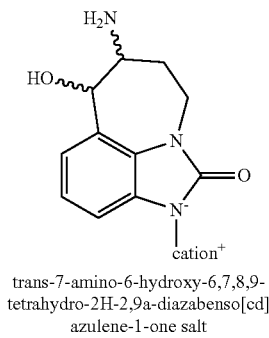

trans-7-amino-6-hydroxy-6,7,8,9-tetrahydro-2H-2,9a-diazabenso[cd]azulene-1-one salt In some such embodiments, for example, the base comprises KOH, and the hydrogenation is conducted in the presence of a catalyst comprising palladium on carbon (Pd/C):

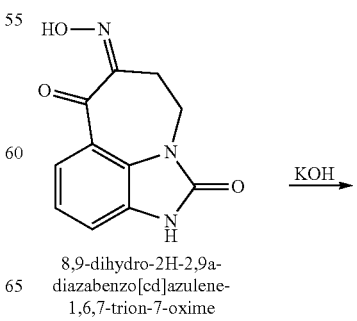

8,9-dihydro-2H-2,9a-diazabenzo[cd]azulene-1,6,7-trion-7-oxime

KOH →

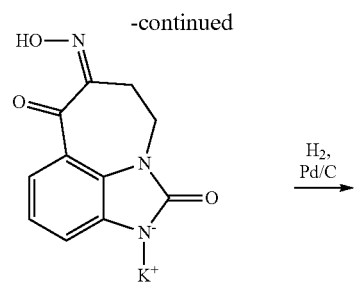

8,9-dihydro-2H-2,9a-
diazabenzo[cd]azulene-1,6,7-
trion-7-oxime potassium salt

H₂, Pd/C →

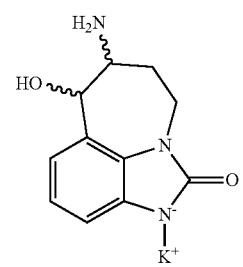

trans-7-amino-6-hydroxy-6,7,8,9-
tetrahydro-2H-2,9a-diazabenso[cd]
azulene-1-one potassium salt In some embodiments, concentration of 8,9-dihydro-2H-2,9a-diazabenzo[cd]azulene-1,6,7-trion-7-oxime reagent at the beginning of the above hydrogenation is at least about 0.08 kg/kg. In some such embodiments, for example, the concentration is from about 0.08 to about 0.24 kg/kg or from about 0.16 to about 0.24 kg/kg (e.g., about 0.20 kg/kg).

The base is generally added to the solution while stirring until the solution becomes clear, which typically represents a point at which substantially all (or all) the 8,9-dihydro-2H-2,9a-diazabenzo[cd]azulene-1,6,7-trion-7-oxime is de-protonated to form a salt, which, in turn, goes into solution. In some embodiments, for example, the base is KOH, and the molar ratio of KOH to 8,9-dihydro-2H-2,9a-diazabenzo[cd]azulene-1,6,7-trion-7-oxime reagent is at least about 1.2, such as from about 1.2 to about 2.2 or from about 1.4 to about 1.7 (e.g., about 1.6). The base is typically introduced as part of an aqueous base solution (e.g., an aqueous solution comprising 45% by weight KOH).

Following de-protonation, undissolved 8,9-dihydro-2H-2,9a-diazabenzo[cd]azulene-1,6,7-trion-7-oxime reagent and any other impurity may be further removed by, for example, contacting it with activated carbon (charcoal). In such embodiments, the mass ratio of the activated carbon to 8,9-dihydro-2H-2,9a-diazabenzo[cd]azulene-1,6,7-trion-7-oxime reagent (including its salt and any undissolved non-salt) is typically no greater than about 0.13 kg/kg. In some such embodiments, for example, the ratio is from about 0.046 to about 0.056 kg/kg (e.g., about 0.051 kg/kg). Following any such filtration, the activated carbon is typically removed using, for example, filtration and/or centrifugation.

In some embodiments, the mass ratio of hydrogenation catalyst (e.g., Pd/C) to 8,9-dihydro-2H-2,9a-diazabenzo[cd]azulene-1,6,7-trion-7-oxime reagent is at least about 0.01 kg/kg. In some such embodiments, for example, the ratio is from about 0.03 to about 0.13 kg/kg, from about 0.030 to about 0.12 kg/kg, or from about 0.030 to about 0.060 kg/kg (e.g., about 0.040 kg/kg). In some embodiments, additional catalyst may be added to increase the conversion rate and/or increase the amount of conversion. Typically, however, the ratio of catalyst to 8,9-dihydro-2H-2,9a-diazabenzo[cd]azulene-1,6,7-trion-7-oxime reagent is less than 0.13 kg/kg.

In some embodiments, at least of portion (and, in some embodiments, substantially all or all) of the de-protonation and hydrogenation is conducted at a temperature of greater than 25° C., such as from about 30 to about 50° C. or from about 35 to about 45° C. (e.g., about 40° C.). Although these reactions may be conducted atmospheric pressure or lesser or greater pressures, in some embodiments, at least a portion of the two reactions (particularly the hydrogenation reaction) is conducted at a pressure that is greater than atmospheric pressure. This pressure may be, for example, from about 3 to about 10 bar, from about 6 to about 10 bar, or from about 7 to about 9 bar (e.g., about 8 bar).

The reaction time for the hydrogenation reaction will vary, depending on various factors, including, for example, the reagent amounts, temperature, pressure, reactor configuration, and other reaction conditions. It also will depend on the desired conversion. In general, the reaction time in a batch reactor is no greater than about 90 hours. In some embodiments, for example, the reaction time is from about 2.5 to about 90 hours, from about 2.5 to about 50 hours, from about 2.5 to about 24 hours, from about 2.5 to about 5 hours, or from about 2.5 to about 4.5 hours (e.g., about 3.5 hours). Although it is contemplated that shorter reaction times than these ranges may be used, such shorter periods may coincide with less hydrogenation and yield loss. And, although greater reaction times may be used, such longer periods may coincide with, for example, inefficient use of energy resources, equipment, and/or manpower.

After the desired conversion has occurred, the catalyst is typically removed from the product solution via, for example, filtration or centrifugation. The product solution is typically filtered until it is substantially (or, in some embodiments, completely) clear.

In some embodiments, the process comprises combining an aqueous solution of a trans-7-amino-6-hydroxy-6,7,8,9-tetrahydro-2H-2,9a-diazabenzo[cd]azulen-1-one salt with acetone, and then decreasing the pH with acid to cause the amine of the trans-7-amino-6-hydroxy-6,7,8,9-tetrahydro-2H-2,9a-diazabenzo[cd]azulen-1-one salt to form, in situ, an isopropylimino group via a nucleophilic addition-elimination reaction:

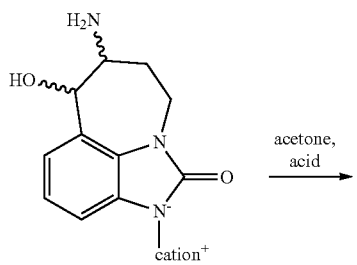

acetone, acid → trans-7-amino-6-hydroxy-
6,7,8,9-tetrahydro-2H-
2,9a-diazabenso[cd]
azulene-1-one salt

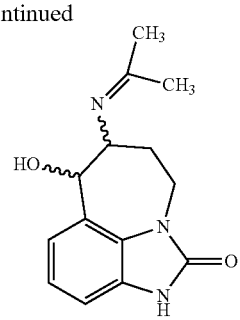

trans-7-[isopropyl imino]-6-hydroxy-6,7,8,9-
tetrahydro-2H-2,9a-diazabenzo[cd]azulen-1-one In some such embodiments, for example, the trans-7-amino-6-hydroxy-6,7,8,9-tetrahydro-2H-2,9a-diazabenzo[cd]azulen-1-one salt is a potassium salt, and the acid is acetic acid:

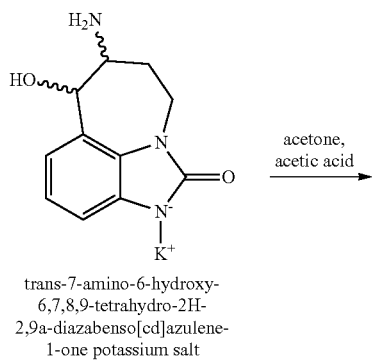

trans-7-amino-6-hydroxy-
6,7,8,9-tetrahydro-2H-
2,9a-diazabenso[cd]azulene-
1-one potassium salt → acetone, acetic acid trans-7-[isopropyl imino]-6-hydroxy-6,7,8,9-
tetrahydro-2H-2,9a-diazabenzo[cd]azulen-1-one In some embodiments, the amount of acid (e.g., acetic acid) introduced into the reaction mixture for the above imine formation is restricted such that it does not reduce the reaction mixture pH to less than about 7.1. In some embodiments, for example, the pH during at least a portion (and, in some such embodiments, substantially all or all) is from about 7.2 to about 7.8, from about 7.3 to about 7.7, or from about 7.4 to about 7.6 (e.g., about 7.5).

In some embodiments, the molar ratio of acetone to trans-7-amino-6-hydroxy-6,7,8,9-tetrahydro-2H-2,9a-diazabenzo[cd]azulen-1-one salt is at least about 1.0. In some such embodiments, the molar ratio is greater than 1.0 (i.e., a molar excess of acetone is used), such as, for example, at least about 4.0. For example, in some such embodiments, the molar ratio is from about 4.0 to about 21, from about 4.5 to about 15, or from about 5 to about 10 (e.g., about 7.5).

In some embodiments, the imine formation is conducted at a temperature of no greater than 40° C. In some embodiments, for example, the reaction is conducted at from about 20 to about 40° C. or from about 25 to about 35° C. (e.g., about 30° C.). In some embodiments, the trans-7-amino-6-hydroxy-6,7,8,9-tetrahydro-2H-2,9a-diazabenzo[cd]azulen-1-one salt solution is at such a temperature before the acetone and/or acetic acid are added. The imine formation may be conducted over a range of pressures, including atmospheric pressure, less than atmospheric pressure, and greater than atmospheric pressure. Typically, however, it is conducted at about atmospheric pressure.

In some embodiments, the process of this invention comprises hydrogenating trans-7-[isopropylimino]6-hydroxy-6,7,8,9-tetrahydro-2H-2,9a-diazabenzo[cd]azulen-1-one in the presence of a catalyst:

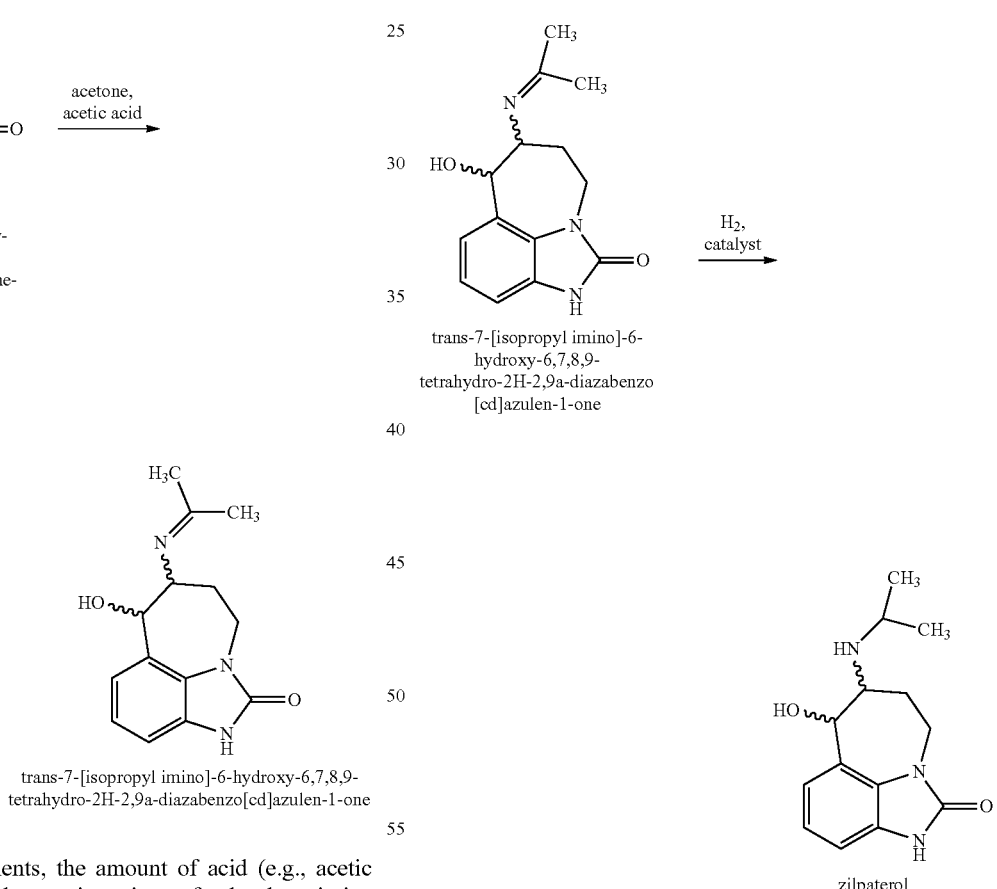

In some embodiments, the hydrogenation is conducted in the presence of a catalyst comprising platinum on a carbon support (Pt/C). In some embodiments, the hydrogenation follows the formation of trans-7-[isopropylimino]6-hydroxy-6,7,8,9-tetrahydro-2H-2,9a-diazabenzo[cd]azulen-1-one in the presence of acetic acid (HOAc). In those instances, the hydrogenation forms a zilpaterol-HOAc solution. To illustrate, where the catalyst is Pt/C, the reaction is:

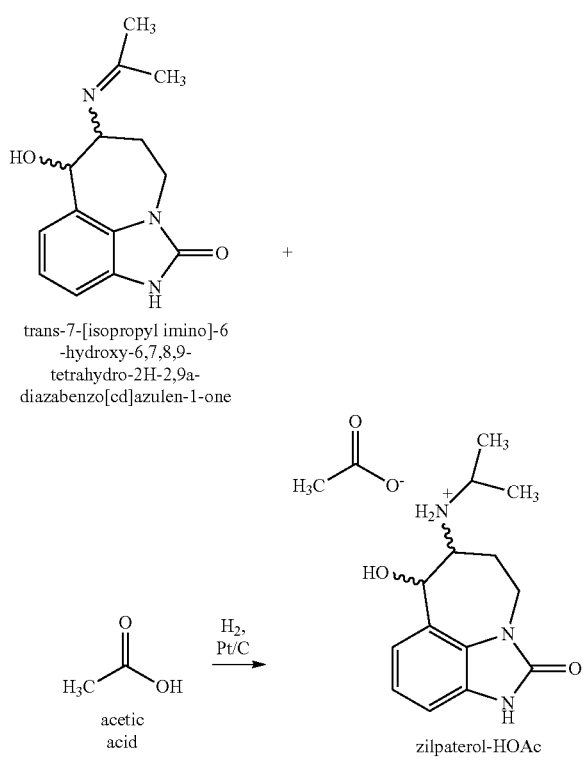

trans-7-[isopropyl imino]-6-hydroxy-6,7,8,9-tetrahydro-2H-2,9a-diazabenzo[cd]azulen-1-one acetic acid zilpaterol-HOAc In some embodiments, the ratio of catalyst (e.g., Pt/C) to trans-7-[isopropylimino]6-hydroxy-6,7,8,9-tetrahydro-2H-2,9a-diazabenzo[cd]azulen-1-one in the above hydrogenation is at least about 0.01 kg/kg. In some such embodiments, for example, the ratio is from about 0.02 to about 0.09 kg/kg, from about 0.02 to about 0.07 kg/kg, or from about 0.02 to about 0.05 kg/kg (e.g., about 0.03 kg/kg). In some embodiments, additional catalyst may be added to increase the conversion rate and/or increase the amount of conversion. Typically, however, the ratio of catalyst to trans-7-[isopropylimino]6-hydroxy-6,7,8,9-tetrahydro-2H-2,9a-diazabenzo[cd]azulen-1-one reagent is less than 0.10 kg/kg.

In some embodiments, at least of portion (and, in some embodiments, substantially all or all) of the hydrogenation is conducted at a temperature of greater than 25° C., such as from about 60 to about 80° C. or from about 65 to about 75° C. (e.g., about 70° C.). In some embodiments, the reaction mixture is heated to such a temperature over a time period that includes an initial portion of the hydrogenation. In such embodiments, this heating may begin before, at the beginning of, or shortly after the beginning of the hydrogenation.

Although the hydrogenation may be conducted at atmospheric pressure or lesser or greater pressures, in some embodiments, at least a portion of the hydrogenation is conducted at a pressure that is greater than atmospheric pressure. This pressure may be, for example, from about 3 to about 10 bar, from about 6 to about 10 bar, or from about 7 to about 9 bar (e.g., about 8 bar).

The reaction time for the hydrogenation reaction will vary, depending on various factors, including the reagent amounts, temperature, pressure, reactor configuration, and other reaction conditions. It also depends on the desired conversion. In general, the reaction time in a batch reactor will be no greater than about 140 hours. In some embodiments, for example, the reaction time is from about 5 minutes to about 140 hours, from about 0.5 to about 50 hours, from about 0.5 to about 24 hours, from about 0.5 to about 5 hours, or from about 1.5 to about 3.5 hours (e.g., about 2.5 hours). Although it is contemplated that shorter reaction times than these ranges may be used, such periods may coincide with less hydrogenation and yield loss. And, although greater reaction times may be used, such longer periods may coincide with, for example, inefficient use of energy resources, equipment, and/or manpower.

In some embodiments, after the desired conversion has occurred, acid is introduced to the product mixture to reduce the pH. In some embodiments, the acid comprises acetic acid. In general, acid is added until the pH is decreased to less than about 7.5. In some such embodiments, for example, acid is added until the pH is from about 5.0 to about 7.4, from about 6.0 to about 7.4, from about 6.5 to about 7.0, or from about 6.5 to about 6.9 (e.g., about 6.8). In some embodiments, the temperature of the product mixture is decreased before and/or during such acid addition. In some such embodiments, the temperature is decreased to a temperature that is no greater than about 40° C. In some such embodiments, for example, the temperature is decreased to a temperature of from about 20 to about 40° C. or from about 26 to about 35° C. (e.g., about 30° C.).

The catalyst is typically removed from the product solution via, for example, filtration or centrifugation. In some embodiments, the catalyst is washed with water or an aqueous acid solution, such as an aqueous acetic acid solution (e.g., a solution comprising 7% acetic acid by weight). The solution used to wash the catalyst may be reintroduced into the product solution. In some embodiments, the product solution is filtered until the solution is substantially (or, in some embodiments, completely) clear.

After the catalyst has been removed, zilpaterol free base is precipitated. This may be achieved by one or more various precipitation methods. In some embodiments, for example, the precipitation comprises increasing the pH of the product mixture. In general, the pH of the product mixture is increased by adding base. Various bases may be used. Typically, the base is added in the form of an aqueous solution. In some embodiments, the base comprises NaOH (e.g., an aqueous solution comprising from about 25 to about 30% by weight NaOH). In some embodiments, sufficient base is added to increase the pH to at least about 9.7. In some such embodiments, for example, the amount of base is sufficient to increase the pH to at least about 10 or at least about 11. In some embodiments, the temperature of the product mixture during the base addition is greater than 25° C. In some such embodiments, for example, the temperature is from about 45 to about 60° C. (e.g., about 50° C.).

In some embodiments, precipitation of the zilpaterol free base also includes concentrating the product mixture by, for example, distillation. In some such embodiments, this occurs before the pH is increased. In general, acetone is first distilled off, which may be followed by distilling off a portion of the water. The amount of volume reduction will depend on, for example, the concentration of zilpaterol base in the product mixture. In some embodiments, the volume of the product mixture is decreased to less than a temperature of about 90% of its initial volume. In some such embodiments, for example, the volume is decreased to from about 65 to about 75% of its initial volume (e.g., to about 70% of its initial volume). Typically, the volume reduction is less than about 50%.

In some embodiments, to partially or completely prevent lump formation of zilpaterol free base solids, an alkylalcohol is added. In some embodiment, the alkylalcohol is ethanol.

Typically, at least a portion (and, more typically, all) of the alcohol is added before the pH of the product mixture is decreased to precipitate the zilpaterol free base. The amount of alcohol may vary. In some embodiments, for example, the ratio of alcohol (e.g., ethanol) to zilpaterol free base is at least about 0.15 l/mol. In some such embodiments, for example, the ratio is from about 0.17 to about 0.65 l/mol, from about 0.2 to about 0.5 l/mol, or from about 0.25 to about 0.38 l/mol (e.g., about 0.30 l/mol).

After at least a portion (and, in some embodiments, substantially all or all) the base has been added, the product mixture is typically permitted to cool to a temperature of no greater than about 25° C. In some embodiments, for example, the mixture is cooled to a temperature of from about −5 to about 15° C. (e.g., about 0° C.).

The zilpaterol free base can be recovered using various separation techniques including, for example, filtration or centrifugation. In some embodiments, the solids are further washed, typically with water. The amount of wash solution will depend on, for example, the impurity concentration in the solids. In some embodiments, the ratio of water to zilpaterol free base is at least about 0.8 l/mol, such as from about from about 0.8 to about 1.6 l/mol, from about 0.85 to about 0.12 l/mol, or from about 0.85 to about 0.10 l/mol (e.g., about 0.9 l/mol).

The above reactions may generally be conducted with various types of reactors. The surface of any such reactor preferably is stable when exposed to the reaction conditions in the reactor. Such reactors may include, for example, glass and glass-lined reactors.

Other reactors may include, for example, stainless steel or other corrosion-resistant metal alloy reactors.

B. Salts

As noted above, this specification describes the use of the invention to make crystalline zilpaterol hydrochloride. The principles in the discussion, however, are generally adaptable for preparing other zilpaterol salts, particularly acid addition salts. A particular salt may be advantageous over other salts due to one or more of its chemical or physical properties, such as stability in differing temperatures and humidities, or a desirable solubility in water, oil, or other solvent. In some embodiments (particularly where the salt is intended for administration to an animal), the salt is pharmaceutically acceptable. The term "pharmaceutically acceptable" is used to characterize the salt as being appropriate for use in a pharmaceutical product. In general, a pharmaceutically acceptable salt has one or more benefits that outweigh any deleterious effect that the salt may have.

Examples of contemplated inorganic acids (besides HCl) that may be used to form acid addition salts include hydrobromic, hydroiodic, nitric, carbonic, sulfuric, and phosphoric acid. Examples of organic acids include, for example, aliphatic, cycloaliphatic, aromatic, araliphatic, heterocyclic, carboxylic, and sulfonic classes of organic acids. Specific examples of organic salts include cholate, sorbate, laurate, acetate, trifluoroacetate, formate, propionate, succinate, glycolate, gluconate, digluconate, lactate, malate, tartaric acid (and derivatives thereof, e.g., dibenzoyltartrate), citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate (and derivatives thereof), embonate (pamoate), ethanesulfonate, benzenesulfonate, pantothenate, 2-hydroxyethanesulfonate, sulfanilate, cyclohexylaminosulfonate, algenic acid, (β-hydroxybutyric acid, galactarate, galacturonate, adipate, alginate, butyrate, camphorate, cam phorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

C. Uses of Zilpaterol and Salts Thereof Prepared in Accordance with this Invention Compositions comprising (or made from) a crystalline zilpaterol salt prepared in accordance with this invention may generally be used, for example, to increase the rate of weight gain, improve feed efficiency, and/or increase carcass leanness in livestock, poultry, and/or fish.

Typically, the zilpaterol salt composition is administered orally. In some embodiments, the composition is added to the intended recipient animal's drinking water. In other embodiments, the zilpaterol salt is added to the intended recipient's feed, either directly or as part of a premix. Suitable oral dosage forms include, for example, solid dosage forms (e.g., tablets, hard or soft capsules, granules, powders, etc.), pastes, and liquid dosage forms (e.g., solutions, suspensions, emulsions, syrups, etc.). These dosage forms optionally comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). Liquid compositions will generally comprise a solvent. The solvent preferably has sufficient chemical properties and quantity to keep the zilpaterol salt solubilized at temperatures at the normal storage temperature for the composition. In some instances, it may be desirable for the compositions to comprise one or more preservatives. The presence of a preservative may, for example, allow for the compositions to be stored over a greater amount of time.

In some embodiments, the crystalline zilpaterol salt is in the form of particles adhered to a support, which, in turn, is fed to the intended recipient animal. The supported crystalline zilpaterol salt may be incorporated into the intended recipient's feed, either directly or as part of a premix. Contemplated supports include, for example, insert supports, such as calcium carbonate, limestone, oyster shell flour, talc, soybean hulls, soybean meal, soybean feed, soybean mill run, wheat middlings, rice hulls, corn meal, corn germ meal, corn gluten, starch, sucrose, and lactose. Particularly contemplated supports include corn cob supports, such as the support discussed in U.S. Pat. No. 5,731,028. In some embodiments employing a corn cob support, the size of the support is from about 300 to about 800 μm.

It is therefore important, that the crystalline zilpaterol salt particles that are adhered to the support have a particle size that is less than the size of the support. Thus, for example, in some embodiments in which the support is from about 300 to about 800 μm, the particles (or at least about 99.5% of the particles) are less than about 300 μm. In some embodiments, the particles (or at least about 90% of the particles) are less than about 200 μm. In some embodiments, the sizes of the majority of the particles are from about 50 to about 200 μm.

As used herein, particle size refers to a number particle size as measured by conventional particle size measuring techniques well known to those skilled in the art, such as laser scattering, sedimentation field flow fractionation, photon correlation spectroscopy, or disk centrifugation.

The particle size measurement indicated as Particle Size Distribution (relative amounts of particles present, sorted according to size) can be e.g. performed with a Malvern Mastersizer 2000 with the Hydro 2000G measuring cell, or with a Horiba LA-910 laser scattering particle size distribution analyzer.

To avoid generating dust when making the supported crystalline zilpaterol salt, it is desirable to avoid using extremely small crystalline zilpaterol salt particles. In some embodiments, for example, the crystalline zilpaterol salt particle size distribution is such that less than about 5% of the crystalline zilpaterol salt particles have particle sizes of less than about 15 μm.

To the extent the composition is incorporated into feed, the feed mixture will vary depending on, for example, the type (e.g., species and breed), age, weight, activity, and condition of the intended recipient. For bovine and swine, various feeds are well known in the art, and often comprise cereals; sugars; grains; arachidic, tournsole, and soybean press cake; flours of animal origin, such as fish flour; amino acids; mineral salts; vitamins; antioxidants; etc. In general, the zilpaterol salt composition can be incorporated into any feed that is available and used for the intended recipient animal.

It is contemplated that the zilpaterol salt composition may be administered via non-oral routes, such as rectally, via inhalation (e.g., via a mist or aerosol), transdermally (e.g., via a transdermal patch), or parenterally (e.g., subcutaneous injection, intravenous injection, intramuscular injection, implanted device, partially implanted device etc.). In some particular embodiments, the composition is administered via an implant, such as a subcutaneous implant. For administration to bovine or swine animals, for example, the composition may be administered in the form of an implant behind the ear.

In general, the zilpaterol salt composition is administered in a dosage form that provides an effective amount of the zilpaterol salt. This is particularly true where the zilpaterol salt is the only active ingredient in the composition. To the extent the zilpaterol salt is administered with another active ingredient(s), the dosage preferably comprises an amount of the zilpaterol salt that, together with the amount of other active ingredient(s), constitutes an effective amount. In the context of a zilpaterol salt, an "effective amount" is an amount sufficient to increase the rate of weight gain, improve feed efficiency, and/or increase carcass leanness in the intended recipient (typically livestock, poultry, and/or fish).

When the composition is orally administered, it is typically preferred to use a daily dosage form. The preferred total daily dose of the zilpaterol salt is typically greater than about 0.01 mg/kg (i.e., milligram of zilpaterol salt per kilogram body weight), particularly for bovine and swine animals. In some such embodiments, the daily dose is from about 0.01 to about 50 mg/kg, from about 0.01 to about 10 mg/kg, from about 0.05 to about 2 mg/kg, from about 0.1 to about 1, or from about 0.1 to about 0.2 mg/kg. To illustrate, in some embodiments, the dose is about 0.15 mg/kg.

In some embodiments where the zilpaterol salt is administered in the recipient animal's feed, the concentration of the zilpaterol salt in the feed (on a 90% dry matter basis) is at least about 0.01 ppm (by weight). For bovine animals, the zilpaterol salt concentration is preferably no greater than about 75 ppm (by weight). In some embodiments, for example, the zilpaterol salt concentration is no greater than about 38 ppm, from about 0.5 to about 20 ppm, from about 3 to about 8 ppm, or from about 3.7 to about 7.5 ppm (by weight). For swine animals, the zilpaterol salt concentration is preferably no greater than about 45 ppm (by weight). In some such embodiments, for example, the concentration is no greater than about 23 ppm, from about 0.5 to about 20 ppm, from about 2 to about 5 ppm, or from about 2.2 to about 4.5 ppm (by weight).

Although single oral daily doses are typically preferred, it is contemplated that shorter or longer periods between doses can be used, depending on, for example, the recipient's metabolism of the zilpaterol salt. It is contemplated that smaller doses may be administered two or more times per day to achieve the desired total daily dose. Such multiple doses per day may, in some instances, be used to increase the total oral daily dose, if desired.

When administered via a subcutaneous implant, the preferred total daily dose of the zilpaterol salt is typically greater than about 0.05 mg/kg (i.e., milligram of zilpaterol salt per kilogram body weight), particularly for bovine and swine animals. In some such embodiments, the daily dose is from about 0.1 to about 0.25 mg/kg.

If the zilpaterol salt composition is administered parenterally via an injection, the concentration of the zilpaterol salt in the dosage form preferably is sufficient to provide the desired therapeutically effective amount of the zilpaterol salt in a volume that is acceptable for parenteral administration. As with oral feeding, an injection dosage form may be administered once per day, although it is contemplated that shorter or longer periods between doses also could be used.

Factors affecting the preferred dosage regimen may include, for example, the type (e.g., species and breed), age, size, sex, diet, activity, and condition of the intended recipient; the type of administration used (e.g., oral via feed, oral via drinking water, subcutaneous implant, other parenteral route, etc.); pharmacological considerations, such as the activity, efficacy, pharmacokinetic, and toxicology profiles of the particular composition administered; and whether the zilpaterol salt is being administered as part of a combination of active ingredients. Thus, the preferred amount of the zilpaterol salt can vary, and, therefore, can deviate from the typical dosages set forth above. Determining such dosage adjustments is generally within the skill of those in the art using conventional means.

It is contemplated that the zilpaterol salt composition may be administered to the intended recipient a single time. In general, however, the composition is administered over time. In some embodiments where the animal recipient is a livestock animal, for example, the zilpaterol salt is administered daily for at least about 2 days, more typically daily for from about 10 to about 60 days, and still more typically daily for from about 20 to about 40 days. In some particular embodiments, the composition is administered daily for from about the last 10 to about the last 60 days of the finishing period, or from about the last 20 to about the last 40 days of the finishing period. The term "finishing period" refers to the later stage of the growing period for an animal. During this period, livestock animals are typically confined in a feedlot. In some embodiments where the livestock animal is a bovine animal, this period lasts for from about 90 to about 225 days, and depends on, for example, the starting body weight of the animal. There is typically a withdrawal period following the finishing period in which no zilpaterol salt thereof is administered. The length of this withdrawal period may depend on, for example, the type (e.g., species and breed), age, weight, activity, and condition of the recipient animal, as well as the maximum acceptable residue concentration in the meat of the animal.

EXAMPLES

The following examples are merely illustrative of embodiments of the invention, and not limiting to the remainder of this disclosure in any way.

Example 1

Preparation of 8,9-dihydro-2H-7H-2,9a-diazabenzo[cd]azulene-1,6-dione

Part A. Preparation of chloro 2,3-dihydro-2-oxo-1H-benzimidazol-1-butanoate.

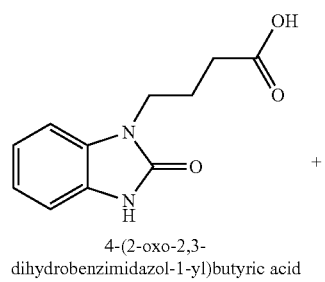
4-(2-oxo-2,3-dihydrobenzimidazol-1-yl)butyric acid

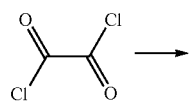

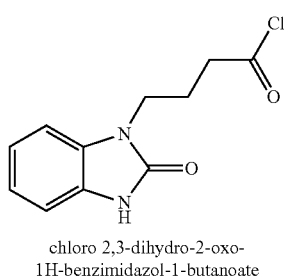
chloro 2,3-dihydro-2-oxo-1H-benzimidazol-1-butanoate

Dichloromethane (3772 L) and then 4-(2-oxo-2,3-dihydrobenzimidazol-1-yl)butyric acid (525 kg; 2.4 kmol) were charged to a stirred-tank reactor, followed by N,N-dimethylformamide (21 L). The resulting mixture was cooled to 10° C. Afterward, oxalyl chloride (326.8 kg)) was dosed at 10-15° C. over 2-3 hours while stirring. The resulting mixture was then stirred at 15-20° C. for an additional 1-3 hours. All the above steps were conducted under a $N_2$ atmosphere. Conversion was checked by in-process control ("IPC").

Part B. Preparation of 8,9-dihydro-2H,7H-2,9a-diazabenzo[cd]azulene-1,6-dione.

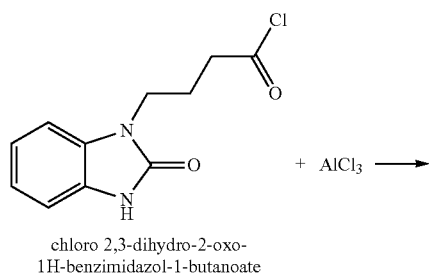
chloro 2,3-dihydro-2-oxo-1H-benzimidazol-1-butanoate

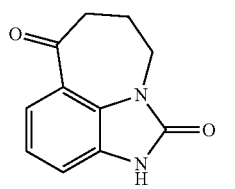
8,9-dihydro-2H,7H-2,9a-diazabenzo[cd]azulene-1,6-dione

Aluminum chloride (1050 kg) and dichloromethane (2403 L) at 10-20° C. were charged to a stirred-tank reactor, followed by additional dichloromethane (112 L) at 10-20° C. to rinse the reactor. The reactor was then pressurized with $N_2$ to 2.7 bar (absolute), and heated to 58-60° C. Next, the product mixture from Part A was added over 2-5 hours. The resulting slurry was stirred for an additional 1-2 hours, and then cooled to 10-20° C. Afterward, the pressure was released. In a second stirred-tank reactor at 5° C., water (3675 L) was charged, followed by aqueous 33% HCl (452 L). This mixture was cooled to 0° C., and the gas in the headspace was evacuated to 270-470 mbar (absolute). About half the content from the first reactor was added to the second reactor at from 5-20° C. The mixture was maintained at 10-30° C. for an additional 30-90 minutes. In parallel to and following the transfer, distillation of dichloromethane occurred. The line between the two reactors was rinsed with dichloromethane (150 ml). The resulting rinse and the contents in the second reactor were transferred to a third stirred-tank reactor. The transfer line between the second and third reactors was rinsed with water (200 L). This rinse also was charged to the third reactor. Water (3675 L) at 5° C. and 33% HCl (452 L) were then added to the second reactor. The resulting mixture was cooled to 0° C., and the pressure in the headspace was set to between 270-470 mbar (absolute). The second half of the content from the first reactor was then added to the second reactor at 5-20° C. This mixture was maintained at 10-30° C. for an additional 30-90 minutes. In parallel to and following the transfer, distillation of dichloromethane occurred. The line between the first and second reactors was rinsed with dichloromethane (150 ml). The resulting rinse and the contents in the second reactor were transferred to the third reactor. The transfer line between the second and third reactors was then rinsed with water (200 L). This rinse was charged to the third reactor. In the third reactor, the dichloromethane was further distilled at 30-40° C. under atmospheric pressure. When the distillation was complete, the suspension was cooled to 0-5° C., and then centrifuged in two parts. Each of the resulting cakes was washed with four times water (390 L for each wash) and once with isopropanol (508 L) at 0-5° C. All the above steps were conducted under a $N_2$ atmosphere.

Example 2

Preparation of 4,5-dihydro-imidazo[4,5,1-jk][1]benzazepin-2,6,7[1H]-trione-6-oxime

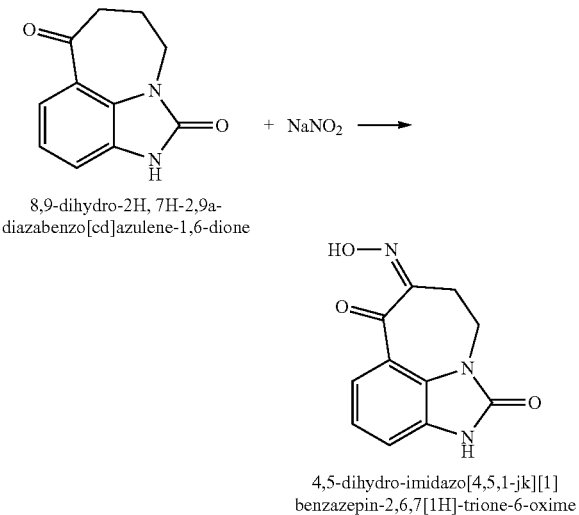

At 20° C., N,N-dimethylformamide (7068 L) was charged to a stirred-tank reactor, followed by 8,9-dihydro-2H,7H-2,9a-diazabenzo[cd]azulene-1,6-dione (450 kg total wet material, approximately 405 kg pure) prepared in accordance with the procedure in Example 1. The addition funnel was rinsed with N,N-dimethylformamide (105 L), and the rinse was charged to the reactor. The resulting mixture was heated at 45° C. until all the 8,9-dihydro-2H,7H-2,9a-diazabenzo[cd]azulene-1,6-dione was in solution. IPC was used to check the amount of pure 8,9-dihydro-2H,7H-2,9a-diazabenzo[cd]azulene-1,6-dione in the mixture, and, from that measurement (together with the mass of wet 8,9-dihydro-2H,7H-2,9a-diazabenzo[cd]azulene-1,6-dione and N,N-dimethylformamide), the exact amount of 8,9-dihydro-2H,7H-2,9a-diazabenzo[cd]azulene-1,6-dione was calculated, which, in turn, was used to calculate the amounts of N,N-dimethylformamide (17.3 kg/kg), sodium nitrite (0.412 kg/kg) and HCl 33% (0.873 kg/kg). For the duration of the IPC, the mixture was cooled to 20° C. Next, sodium nitrite (167 kg, based on 405 kg 8,9-dihydro-2H,7H-2,9a-diazabenzo[cd]azulene-1,6-dione) was added. The addition funnel was rinsed with N,N-dimethylformamide (105 L), and the rinse was charged to the reactor. The temperature was then increased to 45° C. Subsequently, additional N,N-dimethylformamide was charged in the amount calculated earlier (97 L, based on having a total of 7375 L DMF for 405 kg of 8,9-dihydro-2H,7H-2,9a-diazabenzo[cd]azulene-1,6-dione). Next, the resulting mixture was warmed to 48° C., and then 33% HCl (353 kg, based on the batch size) was added over 1 hour, causing the temperature to increase to 60-65° C. by the end of the addition. The mixture was then stirred at 60° C. for another 30 minutes. Next, the mixture was cooled to 45° C. over 1-2 hours. The resulting mixture was transferred into a second reactor. The first reactor was subsequently rinsed with N,N-dimethylformamide (105 L), and the rinse was charged to the second reactor. Water (2000 L) was then added over a 2-hour period at 38° C. The resulting mixture was cooled to 0° C. over 2-3 hours, and then stirred at that temperature for another 2-8 hours. Afterward, the mixture was centrifuged at 0° C., and the resulting cake was washed with three times with water (810 L each time), washed with acetone (1010 L), and dried at 65° C. under vacuum. All the above steps, except for the IPC, were conducted under a $N_2$ atmosphere.

Example 3

Preparation of Zilpaterol

Part A. Formation of Aminoalcohol Potassium Salt from Ketooxime.

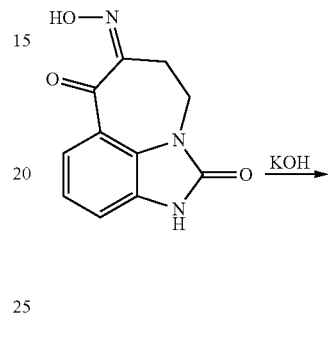

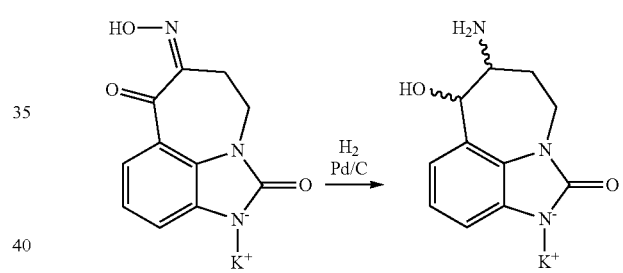

A stirred-tank reactor was purged 3 times with $N_2$ between high pressure (3 bar, absolute) and low pressure (1 bar, absolute) for 10 minutes each. Then a pressure of 0.9 bar (absolute) was established. Water (790 kg) was then charged to the reactor, followed by 4,5-dihydro-imidazo[4,5,1-jk][1]benzazepin-2,6,7[1H]-trione-6-oxime (255 kg) prepared in accordance with Example 2. The reactor contents were then heated to 40° C. Next, 45% KOH (214 kg) was continuously charged to the reactor, causing 4,5-dihydro-imidazo[4,5,1-jk][1]benzazepin-2,6,7[1H]-trione-6-oxime to form the corresponding potassium salt, which, in turn, dissolved (this could be visually verified). The reactor was then charged with active charcoal (13 kg). The resulting mixture was then stirred for 30 minutes at 40° C. The resulting mixture was filtered through a filter loop for one hour to remove the active charcoal. The mixture was then cooled to 15° C. A 5% palladium-on-carbon catalyst (10.9 kg, Johnson-Matthey) was then charged to the reactor. The reactor was then rinsed with water (50 kg). The resulting mixture in the reactor was stirred for 2-3.5 hours at 40° C. and a $H_2$ pressure of 8 bar (absolute). Afterward, the reactor was vented over 30 minutes, and the reaction was analyzed using HPLC. The contents were then filtered in a filter loop for 90 minutes. The filter cake was washed with water (50 L), and removed to recover palladium. The filtered solution was analyzed via HPLC to confirm complete conversion, and then used in the next step.

Part B. Formation of Zilpaterol-HOAc.

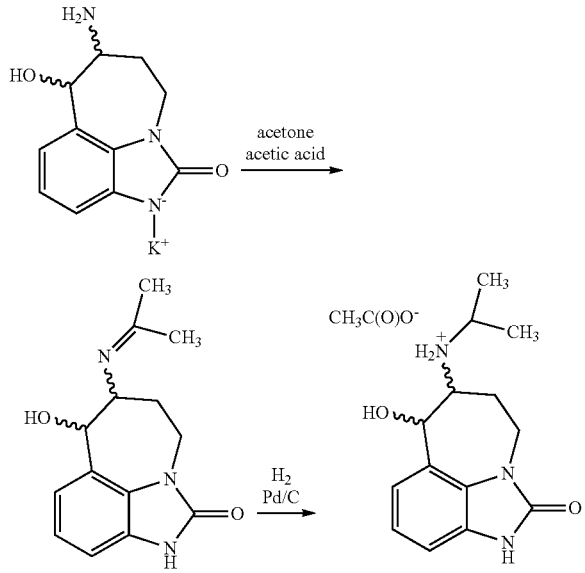

The solution from Part A was cooled to 30° C. Acetone (625 L) was then charged to the reactor. Acetic acid was added to adjust the pH to 7.5. The resulting mixture was then cooled to 15° C. Next, a 5% platinum-on-carbon catalyst (9.4 kg, Degussa) was charged to the reactor, followed by water (50 kg) to rinse the reactor. The head space was purged 3 times with $H_2$ between a high pressure of 5 bar (absolute) and a low pressure of 1 bar (absolute) for 15 minutes each. Then a hydrogen pressure of 8.0 bar (absolute) for hydrogenation was established. The mixture was heated to 70° C. over 1 hour while being stirred, and then maintained at that temperature for an additional 1.5 hours while being stirred. The reactor was then vented, and the headspace was purged with $N_2$. The reaction was analyzed using HPLC. Acetic acid (8 kg) was then charged to the reactor, and the resulting mixture was cooled to 30° C. More acetic acid was added to adjust the pH to 6.8. The mixture was then transferred through a filter loop for 1 hour while being maintained at 30° C. The resulting cake was washed with 7% aqueous acetic acid (75 L). The filtered solution was transferred to another stirred-tank reactor to be used in the next step.

Part C. Formation of Zilpaterol Free Base.

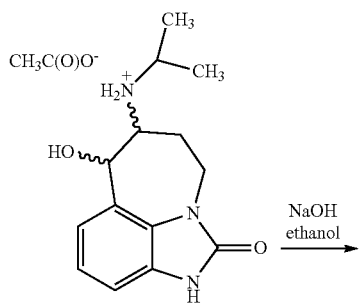

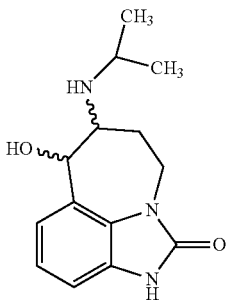

The stirred-tank reactor containing the product from Part B was purged 3 times with $N_2$ between high pressure (2 bar, absolute) and low pressure (1 bar, absolute) for 10 minutes each. Then a pressure of 0.9 bar (absolute) was established. Next, the mixture was concentrated by distillation to about 70%. The concentrated mixture was cooled to 65° C. Ethanol (331 L) was charged to the reactor, and the resulting mixture was cooled to 50° C. The pH was adjusted to 11 using 25-30% NaOH. This caused zilpaterol free base to precipitate. The temperature was decreased to 0° C. to facilitate the precipitation, and maintained at that temperature for an additional hour. The solids were filtered off, and washed with water (700 L).

Example 4a

Synthesis of a Crystalline Zilpaterol HCl Salt

Water (180 kg) was charged to a reactor containing the zilpaterol free base product of Example 3 at a temperature of 10° C. Afterward, a 33% (by weight) HCl solution (126 kg) was added while continuing to maintain the temperature at 10° C. The resulting mixture was heated to 65° C. to dissolve the solids. The reactor headspace was purged 3 times with $N_2$ between high pressure (2 bar, absolute) and low pressure (1 bar, absolute) for 10 minutes each. The resulting solution was filtered until the solution was clear. Afterward, the filter was washed with water (152 kg), which, in turn, was added to the filtered solution. At this point, the zilpaterol hydrochloride concentration in the solution is about 26% by weight. If desirable, water may be added or removed (via, for example, distillation) to obtain the desired concentration.

Once the zilpaterol hydrochloride concentration was determined to be acceptable, polysorbate 60 (18.5 kg) was added. The resulting mixture (in the form of an emulsion) was cooled to 45° C. Zilpaterol hydrochloride monohydrate seed crystals (50 g, in the shape of needles) were charged to the mixture to induce crystallization. The mixture was stirred at a temperature of 45° C. for 15 minutes. The temperature of the resulting white suspension was decreased to a temperature of 21° C. over 90 minutes. Afterward, micronized zilpaterol hydrochloride trihydrate seed crystals (342 g) were charged to transform monohydrate crystals to trihydrate crystals (in the shape of prisms). After 2 hours, the mixture was cooled to 2° C. The solids were separated via centrifugation, and washed with acetone (300 L).

To dry the solids, the headspace in a drier was first purged 3 times with $N_2$ between high pressure (2 bar, absolute) and low pressure (1 bar, absolute) for 10 minutes each. After introducing the solids into the drier, the pressure was reduced to 20 mbar (absolute). The temperature in the drier was then increased to 30° C. The temperature was maintained at 30° C. until the water content in the solids was no greater than 16% (by weight).

Afterward, the temperature was further increased to 60° C. and then maintained at that temperature until the water content in the solids was less than 1% (by weight). The temperature was then decreased to 35° C. The pressure in the drier headspace was then increased to 0.9 bar using $N_2$ over 15 minutes to form the final product which, in turn, was transferred into storage containers.

Example 4b

Synthesis of a Crystalline Zilpaterol HCl Salt

Water (140 kg) was charged to a reactor containing the zilpaterol free base product of Example 3 at a temperature of 10° C. Afterward, a 33% (by weight) HCl solution (126 kg) was added while continuing to maintain the temperature at 10° C. The resulting mixture was heated to 65° C. to dissolve the solids. The reactor headspace was purged 3 times with $N_2$ between high pressure (2 bar, absolute) and low pressure (1 bar, absolute) for 10 minutes each. The resulting solution was filtered until the solution was clear. Afterward, the filter was washed with water (92 kg), which, in turn, was added to the filtered solution. At this point, the zilpaterol hydrochloride concentration in the solution is about 26% by weight. If desirable, water may be added or removed (via, for example, distillation) to obtain the desired concentration.

Once the zilpaterol hydrochloride concentration was determined to be acceptable, polysorbate 60 (18.5 kg) was added. The resulting mixture was cooled to 50° C. Zilpaterol hydrochloride monohydrate seed crystals (50 g, in the shape of needles) were charged to the mixture to induce crystallization. The mixture was stirred at a temperature of 50° C. for 15 minutes (10-20 min). The temperature of the resulting white suspension was decreased to a temperature of 18° C. over 90 minutes. Afterward, micronized zilpaterol hydrochloride trihydrate seed crystals (342 g) were charged to transform monohydrate crystals to trihydrate crystals (in the shape of prisms). After 2 hours (1-15 h), the mixture was cooled to 0° C. The solids were separated via centrifugation, and washed with acetone (300 L).

The solids were dried as shown in Example 4a.

Example 4c

Synthesis of a Crystalline Zilpaterol HCl Salt

Water (140 kg) was charged to a reactor containing the zilpaterol free base product of Example 3 at a temperature of 10° C. Afterward, a 33% (by weight) HCl solution (126 kg) was added while continuing to maintain the temperature at 10° C. The resulting mixture was heated to 65° C. to dissolve the solids. The reactor headspace was purged 3 times with $N_2$ between high pressure (2 bar, absolute) and low pressure (1 bar, absolute) for 10 minutes each. The resulting solution was filtered until the solution was clear. Afterward, the filter was washed with water (92 kg), which, in turn, was added to the filtered solution. At this point, the zilpaterol hydrochloride concentration in the solution is about 26% by weight. If desirable, water may be added or removed (via, for example, distillation) to obtain the desired concentration.

Once the zilpaterol hydrochloride concentration was determined to be acceptable, polysorbate 60 (8 kg) was added. The resulting mixture was cooled to 50° C. Zilpaterol hydrochloride monohydrate seed crystals (50 g, in the shape of needles) were charged to the mixture to induce crystallization. The mixture was stirred at a temperature of 50° C. for 15 minutes (10-20 min). The temperature of the resulting white suspension was decreased to a temperature of 18° C. over 90 minutes. Afterward, micronized zilpaterol hydrochloride trihydrate seed crystals (342 g) were charged to transform monohydrate crystals to trihydrate crystals (in the shape of prisms). After 2 hours (1-15 h), the mixture was cooled to 0° C. The solids were separated via centrifugation, and washed with acetone (300 L).

The solids were dried as shown in Example 4a.

Table 1 shows the Particle Size Distribution (relative amounts of particles present, sorted according to size) of zilpaterol hydrochloride batches produced according to the crystallization process of Examples 4.

TABLE 1

| Batch | Particle size Distribution | | | |
| --- | --- | --- | --- | --- |
| | <=15 µm (%) | >=200 µm (%) | >=250 µm (%) | >=300 µm (%) |
| 1 | 3.0 | 1.0 | 0.1 | 0 |
|   | 3.0 | 1.0 | 0.0 | 0 |
|   | 2.0 | 3.0 | 0.5 | 0 |
| 2 | 4.0 | 4.0 | 0.5 | 0 |
|   | 3.0 | 5.0 | 0.4 | 0 |
|   | 3.0 | 4.0 | 0.4 | 0 |
| 3 | 2.9 | 7.8 | 0.3 | 0 |
|   | 1.6 | 14.3 | 1.7 | 0 |
|   | 3.0 | 11.0 | 0.8 | 0.2 |

Example 5

First Illustration of a Contemplated Suitable Dosage Form

A tablet is prepared containing 2.5 or 5 mg of the crystalline HCl salt of Example 4, and sufficient excipient of lactose, wheat starch, treated starch, rice starch, talc, and magnesium stearate for a final weight of 100 mg.

Example 6

Second Illustration of a Contemplated Suitable Dosage Form

Granules are prepared containing 12.5 or 25 mg of the crystalline HCl salt of Example 6 in each daily dose of granules.

Example 7

Third Illustration of a Contemplated Suitable Dosage Form

Crystalline zilpaterol hydrochloride particles of Example 4 are secured to a 300-800 µm corn cob support to form a premix using the methodology discussed in European Patent 0197188. The concentration of the crystalline zilpaterol HCl salt in the premix is 3% (by weight). At least 95% of the crystal particles have sizes that are greater than 15 µm and less than 250 µm.

Example 8

Fourth Illustration of a Contemplated Suitable Dosage Form

Crystalline zilpaterol hydrochloride particles of Example 4 are secured to a 300-800 μm corn cob support to form a premix using the methodology discussed in European Patent 0197188. The concentration of the crystalline zilpaterol HCl salt in the premix is 3% (by weight). At least 95% of the crystal particles have particle sizes that are greater 15 μm, at least 90% of the crystal particles have a size of less than 200 μm, and at least 99.5% of the crystal particles have a size of less than 300 μm.

The words "comprise," "comprises," and "comprising" in this patent (including the claims) are to be interpreted inclusively rather than exclusively. This interpretation is intended to be the same as the interpretation that these words are given under United States patent law.

The words "process" and "method" are used interchangeably in this patent.

All references cited in this patent are incorporated by reference into this patent.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:

1. A process for making a crystalline zilpaterol salt, wherein the process comprises forming a mixture by combining a surfactant with water and a zilpaterol salt wherein the process further comprises seeding the mixture with crystalline zilpaterol hydrochloride trihydrate crystals after decreasing the temperature.

2. The process according claim 1, wherein:
   a) a zilpaterol salt solution is formed by a process comprising forming a suspension by a process comprising mixing zilpaterol with water, optionally in the presence of an acid solution, and heating the suspension;
   b) the zilpaterol salt solution is mixed with a surfactant;
   c) the mixture is seeded with crystalline zilpaterol hydrochloride trihydrate.

3. The process according to claim 2, wherein the surfactant is a non-ionic surfactant.

4. The process according to claim 2, wherein the acid comprises aqueous hydrochloric acid.

5. The process according to claim 2, wherein the crystalline zilpaterol salt comprises crystalline zilpaterol hydrochloride anhydrate.

6. The process according to claim 2, wherein the mixture has a temperature of from about −5 to about 5° C. for at least a portion of the process in which zilpaterol hydrochloride trihydrate crystals are present.

7. The process according to claim 2, wherein the process further comprises drying a cake comprising zilpaterol hydrochloride trihydrate crystals at a temperature of from about 50 to about 75° C.

8. The process according to claim 2, wherein the mixture is first seeded with zilpaterol hydrochloride monohydrate and then with crystalline zilpaterol hydrochloride trihydrate.

9. The process according to claim 8, wherein the mixture has a temperature of from about 14 to about 25° C. for at least a portion of the process in which zilpaterol hydrochloride monohydrate crystals are present.

10. The process according to claim 2, wherein the zilpaterol hydrochloride crystals have a size distribution in which at least about 95% of the crystal particles have particle sizes that are greater than about 15 μm.

11. The process according to claim 2, wherein the zilpaterol hydrochloride crystals have a size distribution in which at least about 90% of the crystal particles have particle sizes that are less than about 200 μm.

12. The process according to claim 2, wherein the zilpaterol hydrochloride crystals have a size distribution in which at least about 99.5% of the crystal particles have particle sizes that are less than about 300 μm.

13. The process according to claim 2, wherein the process further comprises reacting a salt of trans-7-amino-6-hydroxy-6,7,8,9-tetrahydro-2H-2,9a-diazabenzo[cd]azulen-1-one with acetone in the presence of acetic acid.

14. The process according to claim 13, wherein the trans-7-amino-6-hydroxy-6,7,8,9-tetrahydro-2H-2,9a-diazabenzo[cd]azulen-1-one salt comprises a potassium salt.

15. A process for making a pharmaceutical composition, wherein the process comprises:
   a) preparing a crystalline zilpaterol salt by a process recited in claim 1; and
   b) attaching the crystalline zilpaterol salt to a support.

16. The process according to claim 15, wherein the support comprises discrete particles having sizes of from about 300 to about 800 μm.

17. The process according to claim 15, wherein the support comprises a corn cob support.

18. The process according to claim 15, wherein the crystalline zilpaterol salt comprises crystalline zilpaterol hydrochloride.

19. A method for increasing an animal's rate of weight gain, improving an animal's feed efficiency, and/or increasing an animal's carcass leanness, wherein the method comprises: preparing a crystalline zilpaterol salt by a process recited in claim 1; and
   administering an effective amount of the crystalline zilpaterol salt to the animal.

20. The method according to claim 19, wherein the animal comprises a swine animal.

21. The method according to claim 19, wherein the animal comprises a bovine animal.

22. The method according to claim 19, wherein at least a portion of the crystalline zilpaterol salt is attached to a support.

23. The method according to claim 19, wherein the crystalline zilpaterol salt comprises crystalline zilpaterol hydrochloride.

* * * * *